(12) United States Patent
Daito et al.

(10) Patent No.: US 9,874,655 B2
(45) Date of Patent: Jan. 23, 2018

(54) FLUID ANALYZER USING ABSORPTION SPECTROSCOPY

(71) Applicant: Schlumberger Technology Corporation, Sugar Land, TX (US)

(72) Inventors: Shigeo Daito, Yokohama (JP); Tsutomu Yamate, Yokohama (JP)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 14/886,092

(22) Filed: Oct. 19, 2015

(65) Prior Publication Data

US 2016/0124112 A1 May 5, 2016

Related U.S. Application Data

(60) Provisional application No. 62/073,025, filed on Oct. 31, 2014.

(51) Int. Cl.
| | |
|---|---|
| *G01V 8/12* | (2006.01) |
| *G01N 21/31* | (2006.01) |
| *E21B 49/10* | (2006.01) |

(52) U.S. Cl.
CPC ............. *G01V 8/12* (2013.01); *E21B 49/10* (2013.01); *G01N 21/3103* (2013.01); *G01N 2201/061* (2013.01)

(58) Field of Classification Search
CPC ........................................................ G01V 8/12
USPC ........................................................ 356/436
See application file for complete search history.

(56) References Cited

U.S. PATENT DOCUMENTS

| | | | | |
|---|---|---|---|---|
| 4,562,376 A | * | 12/1985 | Koizumi ............... | H01J 61/523 313/34 |
| 2006/0163483 A1 | * | 7/2006 | Chabanis ............... | B64D 37/32 250/339.12 |
| 2007/0013911 A1 | * | 1/2007 | Difoggio .................. | G01J 3/26 356/436 |
| 2008/0133193 A1 | * | 6/2008 | Gdanski .................. | E21B 43/26 703/10 |
| 2009/0296086 A1 | * | 12/2009 | Appel ................ | G01N 21/3586 356/326 |
| 2010/0091288 A1 | * | 4/2010 | Difoggio .............. | G01N 21/783 356/436 |
| 2011/0023594 A1 | * | 2/2011 | Pelletier ............ | G01N 21/1702 73/152.18 |

(Continued)

*Primary Examiner* — Tarifur Chowdhury
*Assistant Examiner* — Omar Nixon

(57) ABSTRACT

A technique facilitates formation evaluation with downhole devices which may include fluid analyzers having atomic absorption spectroscopy (AAS) systems. According to an embodiment, a fluid analyzer of a downhole tool may be positioned in a wellbore penetrating a subterranean formation. The downhole tool comprises a downhole flowline for receiving a sample fluid. Additionally, the fluid analyzer comprises a flowline positioned to receive the sample fluid for analysis by the atomic absorption spectroscopy system. The atomic absorption spectroscopy system has a light source to generate light and to excite atoms of a substance in the sample fluid. The atomic absorption spectroscopy system also comprises a detector to measure how much light has been absorbed by the substance, thus enabling the atomic absorption spectroscopy analysis.

16 Claims, 6 Drawing Sheets

(56) References Cited

U.S. PATENT DOCUMENTS

| | | | |
|---|---|---|---|
| 2011/0108720 A1* | 5/2011 | Ford | E21B 49/08 |
| | | | 250/262 |
| 2011/0154532 A1* | 6/2011 | Belanger | C07K 14/415 |
| | | | 800/278 |
| 2013/0312956 A1* | 11/2013 | Weston | G01N 21/3577 |
| | | | 166/248 |

* cited by examiner

FIG.10

| Sequence# | Description | Valve #1 | Valve #2 | Vapolization system if using |
|---|---|---|---|---|
| 1 | Normal condition | OPEN | CLOSE | OFF |
| 2 | Sample injection | CLOSE | OPEN | OFF |
| 3 | Prepare for measurement | OPEN | CLOSE | OFF |
| 4 | Attempt measurement | OPEN | CLOSE | ON |
| 5 | Sample cleaning | CLOSE | OPEN | OFF |
| 6 | Normal condition | OPEN | CLOSE | OFF |

FLUID ANALYZER USING ABSORPTION SPECTROSCOPY

CROSS-REFERENCE TO RELATED APPLICATIONS

The present document is based on and claims priority to U.S. Provisional Application Ser. No. 62/073,025 filed Oct. 31, 2014, which is incorporated herein by reference in its entirety.

BACKGROUND

A wellbore may be drilled to locate and produce hydrocarbon-based fluids. The wellbore is drilled by a downhole drilling tool having a drill bit which is advanced into the formation to form a wellbore. As the drilling tool is advanced, drilling mud is pumped through the drilling tool and out through the drill bit to cool the drilling tool and to carry away cuttings. The fluid exits the drill bit and circulates back up to the surface before being recirculated back down to the drilling tool. The drilling mud also may be used to form a mud cake lining the wellbore.

During the drilling operation, various downhole evaluations may be performed to determine characteristics of the wellbore and/or surrounding formation. Depending on the application, the downhole evaluations may be conducted with devices contained in the drilling tool. However, the devices also may be deployed downhole via a wireline after the drilling tool has been removed. Examples of devices employed in performing downhole evaluations may include probes, packers, fluid analyzers, and/or sensors to obtain and measure downhole characteristics which may indicate the presence of hydrocarbons.

SUMMARY

In general, a methodology and system are described for providing improved formation evaluation with a downhole tool having a fluid analyzer. According to an embodiment, the fluid analyzer of the downhole tool comprises an atomic absorption spectroscopy (AAS) system and/or other evaluation systems and may be positioned in a wellbore penetrating a subterranean formation. The downhole tool further comprises a downhole flowline for receiving a sample fluid from the subterranean formation and delivering the sample fluid to the fluid analyzer. The atomic absorption spectroscopy system has a light source to generate light and to excite atoms of a substance, if present, in the sample fluid. The atomic absorption spectroscopy system also comprises a detector to measure how much light has been absorbed by the substance.

However, many modifications are possible without materially departing from the teachings of this disclosure. Accordingly, such modifications are intended to be included within the scope of this disclosure as defined in the claims.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and:

FIG. 10 illustrates an example of a procedure for utilizing an atomic absorption spectroscopy system under a microflow condition, according to an embodiment of the disclosure.

DETAILED DESCRIPTION

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

Embodiments described herein facilitate formation evaluation involving fluid analysis. For example, systems, devices, and methods are described facilitate performance of fluid analysis downhole using atomic absorption spectroscopy. In an example, a fluid analyzer is positioned in a downhole tool which is deployed into a wellbore for measuring properties of downhole fluid drawn into the wellbore and into the downhole tool. In a specific example, the fluid analyzer comprises a flowline, e.g. a primary flowline and/or at least one micro-flowline, combined with an atomic absorption spectroscopy system. A photodetector may be provided in the atomic absorption spectroscopy system to measure atomic absorption at wavelengths used to identify a specific substance or substances in the downhole fluid.

Formation evaluation as used herein relates to the measurement, testing, sampling, and/or other analysis of well site materials such as gases, liquids, and/or solids. Such formation evaluation may be performed at the downhole location and/or at a surface location to provide desired data, e.g. data related to downhole parameters or material properties. Examples of downhole parameters include temperature, pressure, permeability, porosity, and/or other desired parameters. Material properties may comprise properties of the sampled fluid such as viscosity, composition, density, and/or other desired properties. Various downhole parameters and properties may be measured in combination with the atomic absorption spectroscopy analysis.

Fluid analysis as used herein relates to a type of formation evaluation of downhole fluids which may be fluids from the wellbore, formation, reservoir, and/or other fluids located at a well site. Fluid analysis may be performed by a fluid analyzer to detect/measure a substance and sometimes to measure other fluid properties, e.g. viscosity, composition, density, temperature, pressure, flow rate, optical parameters, and/or other desired properties. Fluid analysis may be performed using a variety of systems and devices, as described in greater detail below.

Figure 1:
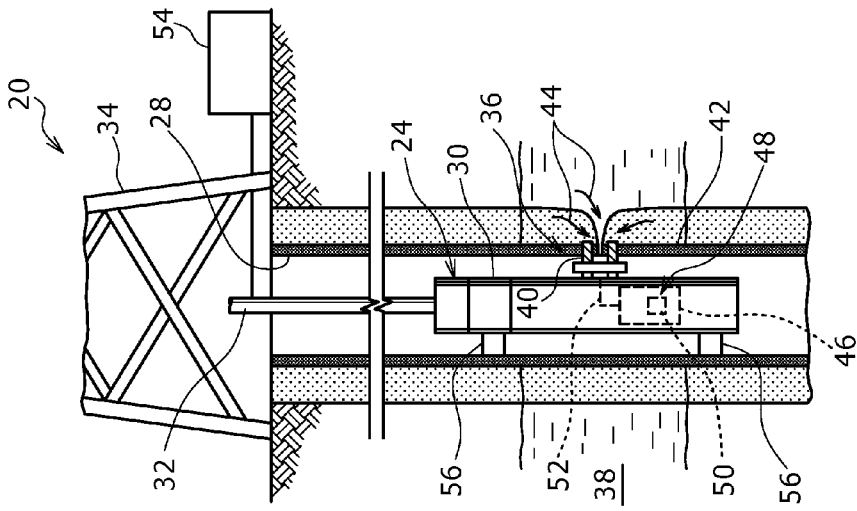
FIG. 1 is a schematic illustration of an example of a downhole drilling tool deployed in a wellbore and including a formation evaluation system for performing a downhole evaluation, according to an embodiment of the disclosure.

Referring generally to FIG. 1, an example of a well system 20 is illustrated. In this example, well system 20 comprises a drill string 22 having a downhole tool 24, e.g. a drilling tool, and a drill bit 26 operated to form a borehole 28, e.g. a wellbore. In some applications, the downhole tool 24 may comprise or may be combined with a while-drilling tool 30, e.g. a measurement-while-drilling (MWD) tool, logging-well-drilling (LWD), and/or other while-drilling tools. The downhole tool 24 may be conveyed downhole via a suitable conveyance 32, e.g. drill pipe, coiled tubing, wireline, supported by surface equipment 34, e.g. a drilling rig.

The downhole tool 24 also comprises a testing system 36 for testing fluids downhole to enable analysis of a surrounding formation 38, e.g. to determine the potential for hydrocarbon production from a reservoir located in formation 38. By way of example, the testing system 36 may comprise a probe 40 adapted to seal with a wall 42 of the wellbore 28 so as to enable drawing of a fluid sample from the surrounding formation 38 and into the downhole tool 24 as represented by arrows 44.

In this example, the testing system 36 comprises a formation evaluation tool 46 having a fluid analyzer 48 for analyzing formation fluid drawn into the downhole tool 24. The fluid analyzer 48 may comprise an atomic absorption spectroscopy system 50 capable of generating and detecting atomic absorption in downhole fluids, as described in greater detail below. The formation evaluation tool 46 also may comprise a flowline 52 for receiving the formation fluid sample from probe 40. The flowline 52 also passes the fluid sample to the fluid analyzer 48 to enable fluid analysis.

A surface control system 54, e.g. a computer-based processing system, may be used to communicate with the downhole tool 24. For example, power signals, command signals, data signals, and/or other types of signals may be communicated between surface unit 54 and downhole tool 24. In some applications, the surface unit 54 may be used to provide power downhole for powering the fluid analyzer 48.

Figure 2:
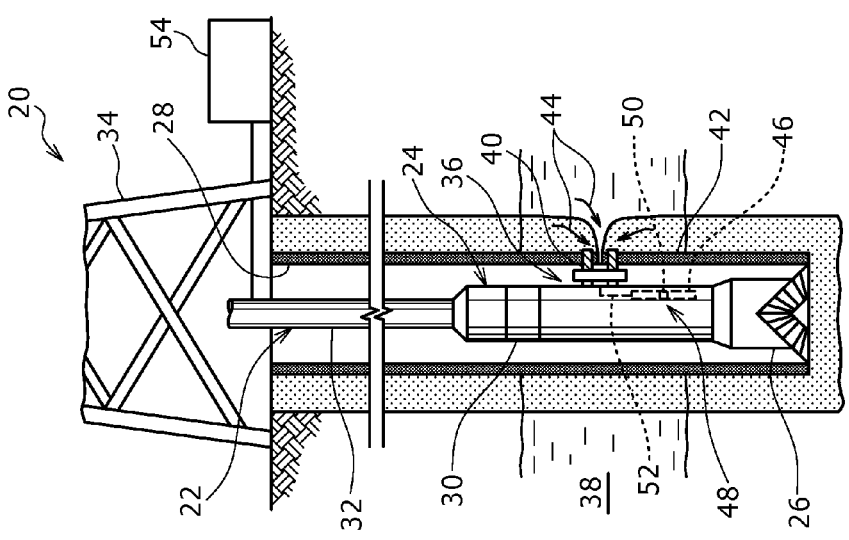
FIG. 2 is a schematic illustration of an example of a downhole wireline tool deployed in a wellbore and including a formation evaluation system for performing a downhole evaluation, according to an embodiment of the disclosure.

Referring generally to FIG. 2, another example of well system 20 is illustrated. In this example, the downhole tool 24 is a wireline tool that may be used for performing formation/fluid evaluation. As illustrated, the downhole wireline tool 24 similarly comprises testing system 36 for testing fluids downhole to enable analysis of a surrounding formation 38, e.g. to determine the potential for hydrocarbon production from a reservoir within formation 38. The testing system 36 may again comprise probe 40 oriented to seal with wall 42 of wellbore 28 so as to enable drawing of a fluid sample from the surrounding formation 38 and into the downhole tool 24 as represented by arrows 44. The conveyance 32 may be in the form of wireline used to lower the downhole wireline tool 24 to a desired position in wellbore 28. In some applications, a backup piston or pistons 56 may be used for pushing the downhole tool 24 and probe 40 against the wellbore wall 42 adjacent formation 38.

In FIGS. 1 and 2, examples of downhole tool 24 are illustrated but other configurations and types of downhole tools may be used to perform formation evaluation. Additionally, various configurations of the fluid analyzer 48 may be combined with the downhole tool 24 to enable testing of various fluid samples and/or formation characteristics. In some applications, the fluid analyzer 48 may be positioned in whole or in part at other suitable locations. For example, portions of the fluid analyzer 48 may be located at the surface, at other downhole locations, and/or at off-site facility locations.

By positioning the testing system 36 and fluid analyzer 48 in the downhole tool 24, real-time data may be collected in situ at downhole conditions. For example, real-time data on temperatures, pressures, sample content, density, flow rate, optical parameters, and/or other data may be collected at downhole conditions by positioning the probe 40 and fluid analyzer 48 where the downhole fluids are located and/or where the fluid sample calibrations are performed. In some applications, fluid samples also may be retrieved and taken to the surface and/or to off-site locations for analysis, e.g. additional analysis. Furthermore, data and test results collected from various locations, e.g. from various wellbores, may be analyzed and compared to further enhance the formation evaluation.

In various analysis procedures, atomic absorption spectroscopy analysis is performed in borehole 28 at downhole tool 24. Atomic absorption spectroscopy is a method for identifying specific substances, e.g. Hg, Pb, Cd, Zn, and/or other substances. Each atom of a given substance has a unique condition of electron potential although the electron normally stays at a ground state. When a light is emitted to the atom, some electrons can be excited by the light if the wavelength of the light is equivalent with a potential difference between the electron ground state and the electron excited state. Hence, a specific substance can be identified and measured by measuring the intensity of the specific wavelength light because the specific wavelength light is absorbed by electron excitement resulting from the unique potential difference of the specific type of atom. In many applications, the substance can be identified and measured in parts per million or even parts per billion using atomic absorption spectroscopy.

To measure atomic absorption, a light source or radiation source with a narrow spectral width is utilized. For example, the light source or radiation source for atomic absorption spectroscopy may have a very narrow spectral width of atomic absorption on the order of, for example, about 0.01 nm. In some applications, the atomic absorption spectroscopy system 50 may utilize an atomic absorption photometer in which a hollow cathode lamp (HCL) can be used. The spectral width of an emission line of a hollow cathode lamp may be even narrower than a line in an atomic absorption spectrum. The atomic absorption spectroscopy system 50 may be implemented in downhole tool 24 to provide a downhole fluid analysis system for identifying and measuring a specific substance received as a fluid sample in a flowline. The atomic absorption spectroscopy system 50 may include or may be combined with a variety of system elements, such as a photodetector which may be connected with a lens, filter, amplifier, and/or other features to facilitate the fluid analysis for a given application.

Figure 3:
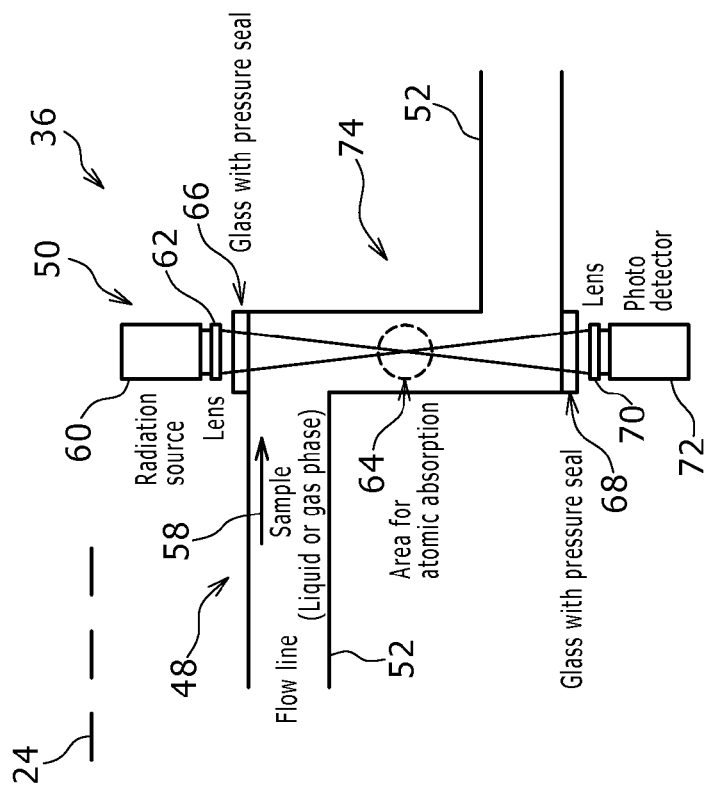
FIG. 3 is a schematic illustration of a portion of a downhole tool having an example of a formation evaluation system including a fluid analyzer with an atomic absorption spectroscopy system, according to an embodiment of the disclosure.

Referring generally to FIG. 3, for example, an embodiment of atomic absorption spectroscopy system 50 is illustrated as incorporated into fluid analyzer 48 of downhole tool 24. In this embodiment, the atomic absorption spectroscopy system 50 of fluid analyzer 48 is positioned for cooperation with flowline 52 which receives a fluid sample from formation 38 via probe 40. The fluid sample is represented by arrow 58 and may comprise liquid and/or gas phases.

The atomic absorption spectroscopy system 50 may comprise a radiation source 60, e.g. a light source, which emits light waves or other suitable radiation. The light waves may be directed through a lens 62 which, in turn, focuses the light waves to an area 64 for atomic absorption. In the illustrated example, the area for atomic absorption 64 is located within flowline 52. As described above, the energy of the light waves focused at area 64 can be used to excite atoms of a specific substance to enable determination of the presence of the specific substance and analysis of its content according to atomic absorption spectroscopy.

As illustrated, the light waves may be directed into flowline 52 through a window 66, e.g. a glass window with a pressure seal. The light energy flows through the area for atomic absorption 64 and out of flowline 52 through a corresponding window 68 having an appropriate pressure seal. The light waves continue to travel through a receiving lens 70 of a photodetector 72. The photodetector 72 may be used to measure atomic absorption, and the atomic absorption data can be used to determine the presence and content of the specific substance or substances. In other words, the photodetector 72 enables atomic absorption spectroscopy analysis by measuring an intensity of a wavelength associated with the substance, thus enabling detection and quantitative analysis of the substance in the fluid sample 58 received in flowline 52. In some applications, the photodetector 72 may work in cooperation with surface system 54 to process the atomic absorption data.

Figure 4:
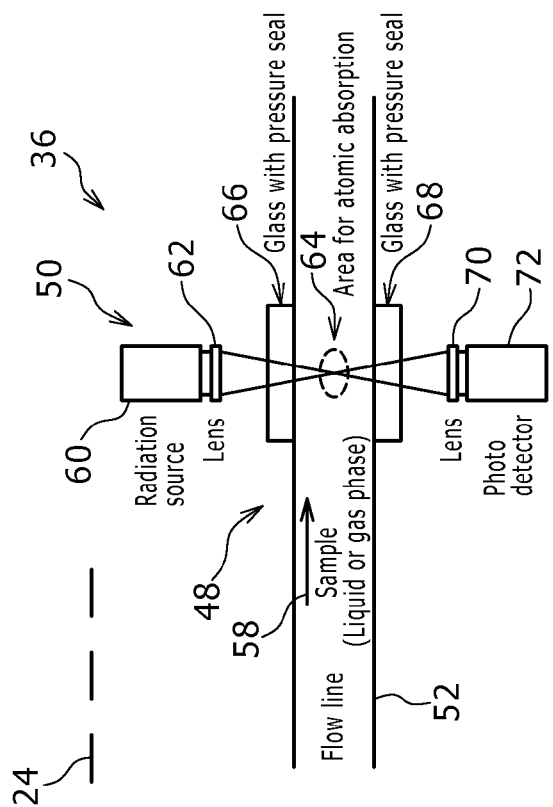
FIG. 4 is a schematic illustration of a portion of a downhole tool having another example of a formation evaluation system including a fluid analyzer with an atomic absorption spectroscopy system, according to an embodiment of the disclosure.

Various arrangements of flowline 52 and atomic absorption spectroscopy system 50 may be constructed to facilitate formation/fluid analysis for a given application. In the embodiment illustrated in FIG. 3, for example, the flowline 52 is routed along a generally linear path and the light energy emitted from radiation source 60 is directed laterally through the flowline 52. In the embodiment illustrated in FIG. 4, however, the flowline 52 extends through an offset portion 74 and the atomic absorption area 64 is disposed along the offset portion 74. This allows the light energy from radiation source 60 to be directed longitudinally, e.g. axially, along the offset portion 74 of flowline 52 and thus over a longer path. The longer path may enhance measurement sensitivity due to an increased chance of the substance absorbing the light during the longer light passage. In other words, the longer length of the passage through which the light passes increases the chances for light absorption by the substance and may induce higher performance of the system due to an improved signal-to-noise ratio.

Figure 5:
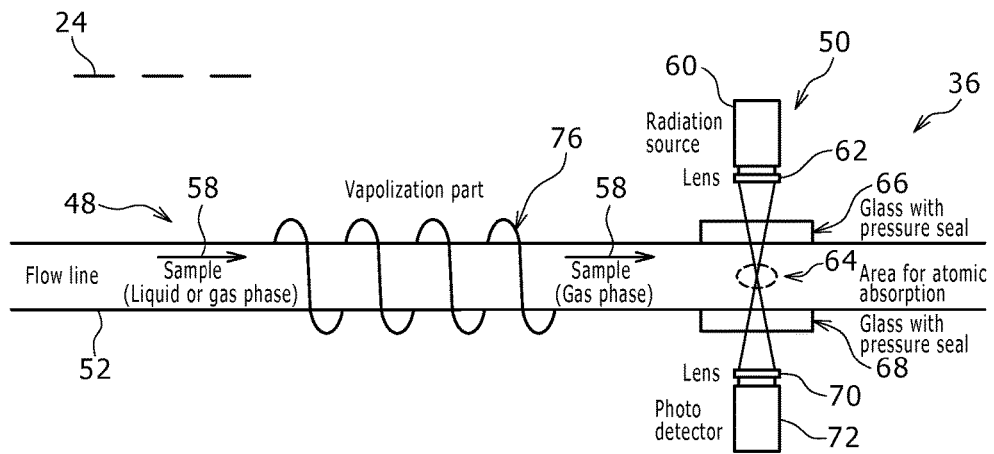
FIG. 5 is a schematic illustration of a portion of a downhole tool having an example of a formation evaluation system including a fluid analyzer with an atomic absorption spectroscopy system and a vaporization system, according to an embodiment of the disclosure.

Referring generally to FIG. 5, another embodiment of testing system 36 and fluid analyzer 48 is illustrated. In this embodiment, the testing system 36 further comprises a vaporization system 76 which vaporizes and/or atomizes sample 58 and works in cooperation with atomic absorption spectroscopy system 50. The vaporization system 76 may be used to change the fluid sample 58 flowing along flowline 52 by, for example, changing a liquid phase to a gas phase. By changing a liquid phase sample to a gas phase sample in some applications, the vaporization system 76 can further help the atomic absorption spectroscopy system 50 determine the presence and amount of a desired substance by enhancing the atomic absorption testing. The vaporization system 76 also may perform as an atomization system or work in cooperation with an atomization system. As further illustrated in FIG. 6, the vaporization system 76 also may be combined with the configuration of atomic absorption spectroscopy system 50 in which the light energy is directed along offset portion 74.

Figure 6:
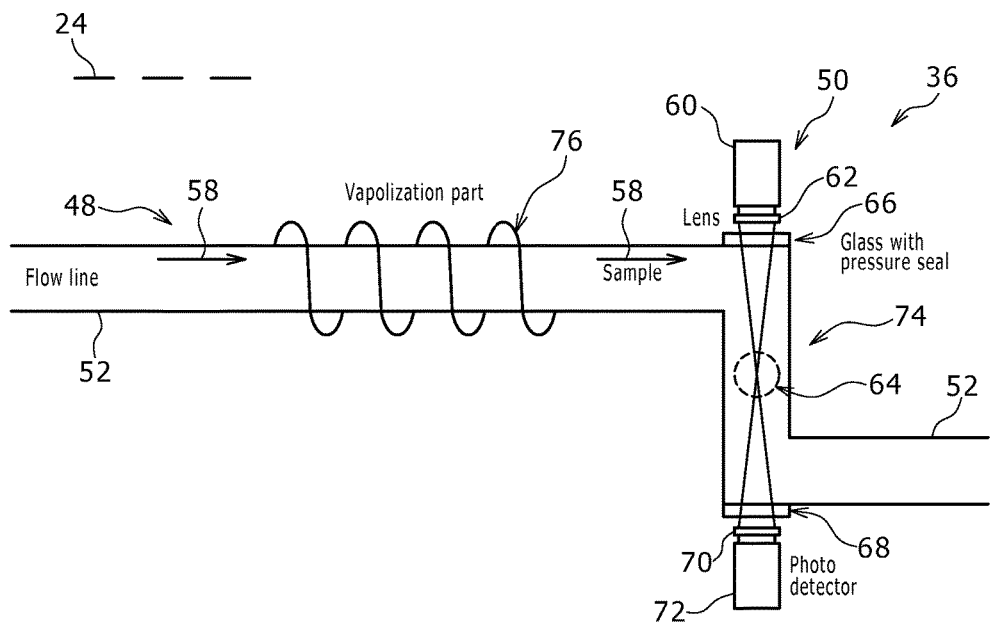
FIG. 6 is a schematic illustration of a portion of a downhole tool having another example of a formation evaluation system including a fluid analyzer with an atomic absorption spectroscopy system and a vaporization system, according to an embodiment of the disclosure.
Figure 7:
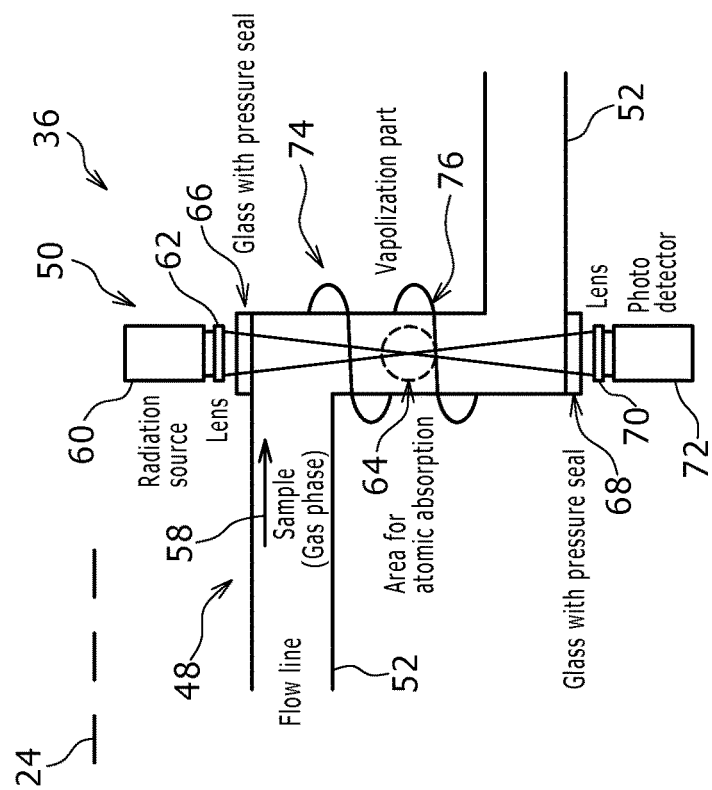
FIG. 7 is a schematic illustration of a portion of a downhole tool having another example of a formation evaluation system including a fluid analyzer with an atomic absorption spectroscopy system and a vaporization system, according to an embodiment of the disclosure.
Figure 8:
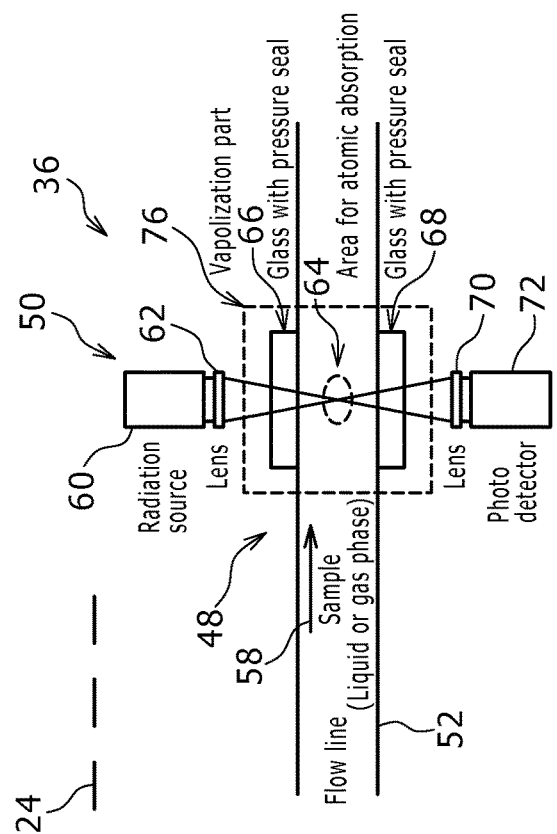
FIG. 8 is a schematic illustration of a portion of a downhole tool having another example of a formation evaluation system including a fluid analyzer with an atomic absorption spectroscopy system and a vaporization system, according to an embodiment of the disclosure.

With respect to the embodiments illustrated in FIGS. 5 and 6, the vaporization/atomization system 76 is located along flowline 52 at a position upstream of the atomic absorption spectroscopy system 50. However, the vaporization system 76 also may be combined with the atomic absorption spectroscopy system 50. As illustrated in FIG. 7, for example, the vaporization system 76 is combined with the atomic absorption spectroscopy system 50 along a linear portion of the flowline 52. In the embodiment illustrated in FIG. 8, another embodiment is provided in which the vaporization system 76 is combined with the atomic absorption spectroscopy system 50 along the offset portion 74 of flowline 52. Depending on the specifics of a given application, the vaporization system 76 may comprise various vaporization devices, such as heating devices, depressurizing devices, and/or other suitable devices to facilitate transition of a liquid phase sample to a gas phase sample. As described above, the vaporization system 76 may function as a vaporization system and/or atomization system.

Figure 9:
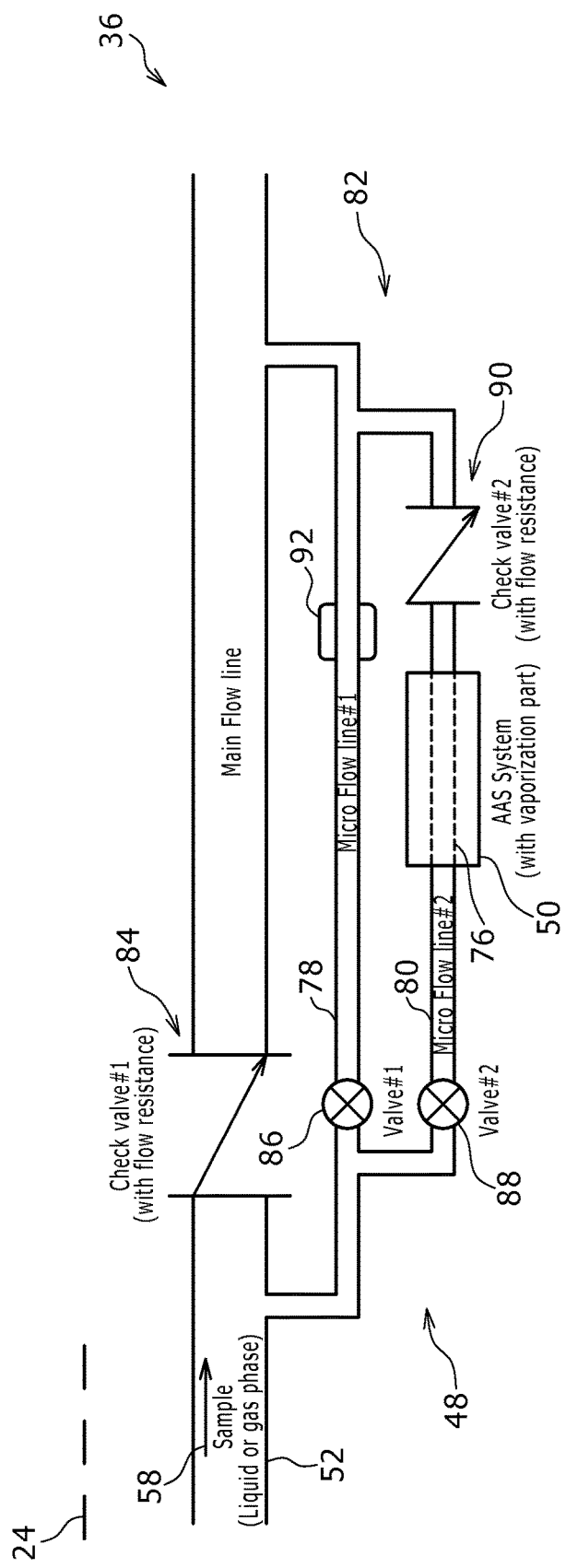
FIG. 9 is a schematic illustration of a portion of a downhole tool having another example of a formation evaluation system including a fluid analyzer with an atomic absorption spectroscopy system, a vaporization system, and a system for inducing flow into the atomic absorption spectroscopy system, according to an embodiment of the disclosure.

Referring generally to FIG. 9, another embodiment of testing system 36 and fluid analyzer 48 is illustrated. In this embodiment, the testing system 36 comprises a plurality of flowlines, e.g. a primary flowline and at least one micro-flowline. By way of example, the testing system 36 comprises a micro-flowline 78 and sometimes a plurality of micro-flowlines 78, 80 which work in cooperation with the primary flowline 52. The atomic absorption spectroscopy system 50, alone or in combination with the vaporization system 76, may be positioned along one of the micro-flowlines. In the specific example illustrated, the atomic absorption spectroscopy system 50 and the vaporization system 76 are positioned along micro-flowline 80. In some applications, the fluid volume for sampling can be very small, e.g. a microliter, so the overall testing system 36 may be constructed with a microfluidics system 82 having micro-flowlines 78, 80.

In operation, sample probe 40 is used to introduce fluid sample 58 along primary flowline 52. A portion of the fluid sample 58 is diverted to the micro-flowlines 78, 80 by, for example, a flow resistance device 84, e.g. a check valve, which provides flow resistance along primary flowline 52. The flow of sample fluid separated from the primary flowline 52 can be controlled as it passes through microfluidics system 82. For example, a controllable first valve 86 disposed along micro-flowline 78 and a controllable second valve 88 disposed along micro-flowline 80 may be selectively actuated to control flow along the micro-flowlines 78, 80. In some applications, a second flow resistance device 90 may be disposed along micro-flowline 80 downstream of atomic absorption spectroscopy system 50.

During testing, the sample fluid 58 may be controllably directed into micro-flowline 80 and through atomic absorption spectroscopy system 50 by opening valve 88 and closing valve 86. In some applications, the fluid sample flowing along micro-flowline 80 also may be subjected to vaporization system 76. A more detailed example of an operational procedure for testing fluid samples is described below and illustrated in the table of FIG. 10.

It should be noted that another sensor system or systems 92 may be disposed along at least one of the flowline 52, micro-flowline 78, and/or micro-flowline 80. By way of example, the sensor system 92 may comprise a gas chromatography system having a small volume sampling and vaporization function. The methodology also may involve identifying different substances within the fluid sample 58 via different types of sensors. In some applications, sensors may be used to detect other optical parameters of light emitted through the downhole fluid sample.

Referring again to FIG. 10, the illustrated table provides a sequence for testing a fluid sample with atomic absorption spectroscopy system 50 and vaporization system 76. In this example, the valve #1 listed in the table corresponds with valve 86 of FIG. 9 and the valve #2 listed in the table corresponds with valve 88 of FIG. 9. During an initial normal condition, valve 86 is open, valve 88 is closed, and vaporization system 76 is off. The fluid sample 58 is then injected into micro-flowline 80 by closing valve 86 and opening valve 88 while the vaporization system 76 remains off. Subsequently, valve 86 is opened and valve 88 is closed to prepare for sample testing, e.g. substance detection and measurement.

During fluid sample testing, valve 86 remains open, valve 88 remains closed, and vaporization and/or atomization system 76 is turned on to, for example, convert liquid sample phase to gas sample phase. After testing, the sample may be cleaned from micro-flowline 80 by closing valve 86 and opening valve 88. While cleaning out the fluid sample, the vaporization and/or atomization system 76 may be shut off. The microfluidic system 82 is then returned to the normal operating condition.

Depending on the specifics of a given application, the downhole tool 24 may comprise various other and/or additional components arranged in desired configurations. Additionally, the sampling procedures may be performed during drilling operations or during various other downhole operations. The sampling probe and related components for obtaining the fluid sample from the surrounding formation may be adjusted according to the structure of the downhole tool and/or environmental parameters. Similarly, the size, components, and configuration of the testing system 36 may be adjusted according to the configuration of the downhole tool 24 and to accommodate various environmental constraints or other parameters. Depending on the application, the atomic absorption spectroscopy system 50 may be used to measure absorption of the light and/or intensity, e.g. fluorescence, of the light.

Although a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

What is claimed is:

1. A system for testing fluids downhole, comprising:
a downhole tool having a fluid analyzer, the fluid analyzer comprising:
a flowline positioned to receive a fluid sample from a surrounding subterranean formation while the downhole tool is positioned in a borehole;
a vaporization system to vaporize and atomize the fluid sample during conversion of the fluid sample from liquid phase to gas phase, wherein the vaporization system comprises a depressuring device;
a light source positioned along the flowline, the light source being oriented to generate light in a direction able to excite metallic atoms of a substance in the fluid sample for atomic absorption spectroscopy; and
a photodetector to enable the atomic absorption spectroscopy by measuring an absorption of a wavelength corresponding with the substance, thus detecting whether the substance is present in the fluid sample received in the flowline,
wherein the light source generates the light with a width of an emission line narrower than a line in an atomic absorption spectrum.

2. The system as recited in claim 1, wherein the fluid analyzer further comprises a microfluidics system to separate a portion of the fluid sample from a primary flowline and to direct the portion through a micro-flowline for atomic absorption spectroscopy analysis.

3. The system as recited in claim 2, wherein the microfluidics system comprises a plurality of the micro-flowlines and a plurality of valves which may be selectively actuated to control flow of fluid along the micro-flowlines.

4. The system as recited in claim 1, wherein the downhole tool comprises a downhole drilling tool.

5. The system as recited in claim 1, wherein the downhole tool is deployed downhole into a borehole via a wireline.

6. The system as recited in claim 1, wherein the light source is oriented to direct the light transversely across the flowline.

7. The system as recited in claim 1, wherein the light source is oriented to direct the light longitudinally along an offset portion of the flowline.

8. The system as recited in claim 1, wherein the vaporization system is disposed upstream from the light source and the photodetector.

9. A method, comprising:
obtaining a fluid sample from a formation surrounding a borehole;
directing the fluid sample along a flowline located downhole in a downhole testing system;
operating a vaporization system to change the fluid sample from a liquid phase to a gas phase for atomization, wherein the vaporization system is deployed with a depressuring device upstream from an atomic absorption spectroscopy system used to perform the atomic absorption spectroscopy on the fluid sample;
using atomic absorption spectroscopy to determine the presence of metallic elements in a specific substance within the fluid sample; and
providing data on the specific substance to a surface control system.

10. The method as recited in claim 9, wherein directing comprises initially directing the fluid sample along a primary flowline and diverting a portion of the fluid sample through a micro-flowline.

11. The method as recited in claim 10, further comprising positioning an atomic absorption spectroscopy system and a vaporization system along the micro-flowline.

12. The method as recited in claim 11, wherein diverting comprises selectively diverting fluid of the fluid sample through the micro-flowline or through another micro-flowline during sequential fluid testing stages.

13. The method as recited in claim 9, wherein using comprises using an atomic absorption spectroscopy system positioned in a downhole drilling tool.

14. A system for testing fluids downhole, comprising:
a downhole tool deployed downhole into a borehole via a conveyance, the downhole tool comprising a fluid analyzer coupled with a probe, the probe being oriented to receive a fluid sample from a formation surrounding the borehole, the fluid analyzer comprising:
a flowline positioned to receive the fluid sample from the probe; and
an atomic absorption spectroscopy system disposed along the flowline, the atomic absorption spectroscopy system using light energy to detect metallic elements of a specific substance in the fluid sample,
wherein the fluid analyzer further comprises a vaporization system to change the fluid sample from liquid phase to gas phase for atomization before entering the atomic absorption spectroscopy system, and
wherein the vaporization system comprises a depressuring device.

15. The system as recited in claim 14, wherein the fluid analyzer further comprises a microfluidics system to separate a portion of the fluid sample from a primary flowline and to direct the portion through a micro-flowline for atomic absorption spectroscopy analysis via the atomic absorption spectroscopy system disposed along the micro-flowline.

16. The system as recited in claim 14, wherein the downhole tool is a downhole drilling tool.

* * * * *